(12) United States Patent
Ishige et al.

(10) Patent No.: US 7,960,113 B2
(45) Date of Patent: Jun. 14, 2011

(54) DNA ANALYSIS METHOD AND DNA ANALYZER

(75) Inventors: Yu Ishige, Tokyo (JP); Masao Kamahori, Kokubunji (JP)

(73) Assignee: Hitachi, Ltd., Tokyo (JP)

( * ) Notice: Subject to any disclaimer, the term of this patent is extended or adjusted under 35 U.S.C. 154(b) by 784 days.

(21) Appl. No.: 12/068,206

(22) Filed: Feb. 4, 2008

(65) Prior Publication Data

US 2009/0166221 A1    Jul. 2, 2009

(30) Foreign Application Priority Data

Mar. 23, 2007    (JP) ................................. 2007-077294

(51) Int. Cl.
- *C12Q 1/68* (2006.01)
- *C12M 1/40* (2006.01)
- *G01N 33/531* (2006.01)

(52) U.S. Cl. .................... 435/6; 204/403.01; 435/287.2; 205/777.5

(58) Field of Classification Search .................. None
See application file for complete search history.

(56) References Cited

U.S. PATENT DOCUMENTS

| | | | | |
|---|---|---|---|---|
| 5,602,000 | A * | 2/1997 | Hyman | 435/91.1 |
| 7,838,226 | B2 * | 11/2010 | Kamahori et al. | 435/6 |
| 2004/0235025 | A1 * | 11/2004 | Mori et al. | 435/6 |
| 2007/0059741 | A1 * | 3/2007 | Kamahori et al. | 435/6 |
| 2008/0314746 | A1 * | 12/2008 | Ishige et al. | 204/403.01 |
| 2009/0142767 | A1 * | 6/2009 | Taniguchi et al. | 435/6 |

FOREIGN PATENT DOCUMENTS

| | | |
|---|---|---|
| JP | 57082769 A | 11/1980 |
| JP | 57082769 A * | 5/1982 |
| JP | 9-500727 | 7/1994 |
| WO | WO 95/03543 | 7/1994 |
| WO | WO 2005/003750 A1 | 7/2004 |
| WO | WO 2005003750 A1 * | 1/2005 |

OTHER PUBLICATIONS

Katherine A. Erickson et al.; "Evaluation of a Novel Point-of-Care System, the i-STAT Portable Clinical Analyzer"; Clinical Chemistry, vol. 39, No. 2, pp. 283-287 (1993).

Marcel Margulies et al., "Genome Sequencing in Microfabricated High-Density Picolitre Reactors", Nature, vol. 437, Sep. 15, 2005, pp. 376-380 and 120.

Toshiya Sakata et al., "DNA Sequencing Based on Intrinsic Molecular Charges", Angew. Chem. Int. Ed. 2006, vol. 45, pp. 2225-2228.

Naonori Inoue et al., "Synthesis and Properties of 4'-ThioDNA: Unexpected RNA-Like Behavior of 4'-ThioDNA", Nucleic Acids Research, 2006, vol. 34, No. 12, pp. 3476-3483.

* cited by examiner

*Primary Examiner* — Nam X Nguyen
*Assistant Examiner* — Kourtney R Salzman
(74) *Attorney, Agent, or Firm* — Stites & Harbison PLLC; Juan Carlos A. Marquez, Esq.

(57) ABSTRACT

Disclosed is a DNA analysis method and a DNA analyzer whose signal intensity is not lowered even when a material at a higher density is measured. There is supplied dATP, dTTP, dGTP, or dCTP from a dATP solution vessel, a dTTP solution vessel, a dGTP solution vessel, or a dCTP solution vessel, and this causes an extension reaction of a double-stranded DNA immobilized to a bead, to yield pyrophosphoric acid. The pyrophosphoric acid is converted into a redox compound by the actions of a reagent and an enzyme contained in a reaction buffer in a reaction buffer vessel. The redox compound causes a variation in surface potential of a measuring electrode bearing an electrochemically active material immobilized thereto through an insulating molecule, and this variation causes a variation in drain current of a field-effect transistor electrically connected to the measuring electrode. Thus, the extension reaction is detected.

9 Claims, 9 Drawing Sheets

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: chemically synthesized

<400> SEQUENCE: 1
cacactcaca gttttcactt                                                    20

<210> SEQ ID NO 2
<211> LENGTH: 30
<212> TYPE: DNA
<213> ORGANISM: Artificial Sequence
<220> FEATURE:
<223> OTHER INFORMATION: chemically synthesized

<400> SEQUENCE: 2
gcatacacta aagtgaaaac tgtgagtgtg                                         30

<210> SEQ ID NO 3
<211> LENGTH: 30
<212> TYPE: DNA
<213> ORGANISM: Artificial Sequence
<220> FEATURE:
<223> OTHER INFORMATION: chemically synthesized

<400> SEQUENCE: 3
gcatacactg aagtgaaaac tgtgagtgtg                                         30

DNA ANALYSIS METHOD AND DNA ANALYZER

CLAIM OF PRIORITY

The present application claims priority from Japanese application JP 2007-077294 filed on Mar. 23, 2007, the content of which is hereby incorporated by reference into this application.

FIELD OF THE INVENTION

The present invention relates to a method and a system that can determine base sequences of DNAs in trace amounts with high sensitivity.

BACKGROUND OF THE INVENTION

With advancing base sequence analysis technologies such as DNA sequencers, complete genome sequences have been analyzed in a variety of biological species such as the human. These analyzed genome sequences belong to specific individuals, and studies on differences in genome sequence among individuals have been launched as the next stage. However, it is difficult to analyze complete genome sequences of respective individuals, because it takes enormous time and cost for the current base sequence analysis technologies to analyze complete genome sequences in an individual-to-individual manner. Demands have therefore been made to provide a base sequence analysis technology that can analyze genome sequences in a short time at low cost. Specifically, DNA sequencers desirably have higher throughputs and analyze samples in smaller amounts.

For enabling DNA sequencers to have higher throughputs, M. Margulies et al. discloses a process using bead handling and pyrosequencing technologies in combination in Nature 437, 376-380 (2005). According to this process, DNA to be analyzed is immobilized to beads, and $45 \times 10^4$ beads are integrated (packed) and concurrently subjected to pyrosequencing. Thus, a base sequencing rate per one base can be increased. The pyrosequencing is a base sequence analysis technology utilizing that pyrophosphoric acid is released when a deoxynucleotide triphosphate (dNTP) is taken into a double-stranded DNA as a result of a synthesis reaction (extension reaction) of the double-stranded DNA catalyzed by a DNA polymerase. A DNA (sample DNA) whose base sequence is to be analyzed is hybridized with a DNA (primer DNA) deciding the start point (origin) of complementary strand synthesis. Four dNTPs (dATPαS, dTTP, dGTP, and dCTP) are sequentially fed to the hybridized DNA in the presence of a DNA polymerase, and, when an extension reaction occurs, pyrophosphoric acid is formed in a number corresponding to the number of extended bases. The formed pyrophosphoric acid is converted to light emission by an enzymatic reaction by the catalysis of luciferase, and the light emission is detected with a photoelectric transducer. The base sequence of the sample DNA can be determined by detecting the presence or absence of an extension reaction and/or determining the quantity of light emission when different dNTPs are added. In this process, dATPαS is generally used as a dNTP instead of dATP, because dATP and ATP are resemble with each other in structure, and background light is not trivial when dATP is used as the dNTP.

On the other hand, electrical DNA sequencings and single nucleotide polymorphism (SNP) typings have been conducted using, for example, field-effect transistor (FET) sensors and pH sensors instead of using optical detection techniques. A DNA sequencer using FET sensors detects an extension reaction by the catalysis of a DNA polymerase as a variation in surface potential (T. Sakata et. al., Angew. Chem. Int. Ed. 45, 2225-2228 (2006)). Specifically, a sample DNA is hybridized with a primer DNA that has been immobilized to a surface of a FET sensor, and four dNTPs (dATPαS, dTTP, dGTP, and dCTP) are sequentially fed thereto in the presence of a DNA polymerase. When an extension reaction occurs, a surface potential of the FET sensor decreases, because phosphates groups in side chain of the DNA have negative charges in an aqueous solution, and when the number of bases of the DNA immobilized to the surface of the FET sensor increases, the amount of negative charges on the surface of the FET sensor increases. By detecting the variation in surface potential using the FET sensor, the base sequence of the sample DNA can be determined.

In a pyrophosphate-detecting sensor using a pH sensor (Japanese Patent No. 3761569), pyrophosphoric acid formed as a result of a nucleic-acid amplification reaction, such as a polymerase chain reaction (PCR), is enzymatically converted into a hydrogen ion, and the increased hydrogen ion is detected with the pH sensor. Whether a polymerase chain reaction (PCR) is detected from how much the pH varies, and a single nucleotide polymorphism (SNP) of a sample DNA is determined.

SUMMARY OF THE INVENTION

One of embodiments of the present invention provides a deoxyribonucleic acid (DNA) analysis method comprising the steps of: providing a sample containing a DNA to be analyzed and a primer hybridized to the DNA; carrying out an extension reaction of the primer in the presence of deoxyribonucleotide triphosphates (dNTPs) and a DNA polymerase so that a primer extension reaction product is formed; converting pyrophosphoric acid formed as a result of the extension reaction into a redox compound; and electrically detecting the redox compound.

And one of embodiments of the present invention also provides a DNA analysis system comprising: a vessel bearing an immobilized nucleic acid or containing an article bearing an immobilized nucleic acid, wherein the vessel is configured to receive a liquid; one or more measuring electrodes that are in contact with the liquid to be contained in the vessel; an electrochemically active material that is immobilized to a surface of the measuring electrode through an insulating molecule; a reference electrode that is in contact with the liquid; one or more potentiometers that measure interface potentials of the one or more measuring electrodes; a first feeder that feeds dATP or an analogue thereof to the vessel; a second feeder that feeds dGTP or an analogue thereof to the vessel; a third feeder that feeds dCTP or an analogue thereof to the vessel; and a fourth feeder that feeds dTTP or an analogue thereof to the vessel.

Pyrosequencers can have higher throughputs by reducing diameters of beads to which primer DNAs are immobilized and using the beads at a higher density. However, when a smaller amount of a sample DNA is used along with an increasing density of the beads, the quantity of light emission decreases, because the pyrosequencing is based on that pyrophosphoric acid formed as a result of a DNA extension reaction is converted to light emission, and the light emission is detected. Specifically, when beads have smaller diameters and used at a higher density, the detection sensitivity is lowered, an expensive detector is required, and the entire system is increased in size and cost. In addition, dATPαS used in pyrosequencers is expensive as much as 100 times the cost of dATP, and this causes increased cost for the base sequence analysis.

DNA sequencers using FETs fundamentally carry out sequencing by measuring potentials and can advantageously maintain their sensitivities even when sample volume decreases. In addition, their FET sensors can be easily integrated at a higher density, because they do not require complicated detection systems. However, a variation in surface potential per one base extension reaction decreases with a proceeding extension reaction of a double-stranded DNA and with an increasing distance between an extension reaction site and the surface of the sensor. This is because the effect of a negative charge on the surface potential varies depending on the distance between the surface of the FET sensor and the charge. Specifically, a detectable base length varies significantly depending on the Debye length, and a detectable base length is about ten bases even in a specially low-concentration buffer (2.5 mM) according to the known technology. The Debye length in this case is about 1 nm, and a theoretical detection limit is about thirty bases in consideration of the size of one base (0.34 nm). Accordingly, it is difficult to use the technology in general sequencing.

In contrast, when pyrosequencing is conducted using a phosphate-detecting sensor including a pH sensor, the sensitivity is not lowered even when sample volume decreases. This is because not the amount but the concentration of pyrophosphoric acid is detected for detecting pyrophosphoric acid formed as a result of a DNA extension reaction. In addition, this sensor is not limited in detectable base length in contrast to the DNA sequencer using FETs and is expected to exhibit a detectable readout base length equivalent to that in pyrosequencing in which light emission is detected. It is difficult, however, to constitute a DNA sequencer using this sensor, because pH may vary by the action of a reagent used in DNA sequencing and pH variation caused by the formed pyrophosphoric acid may be buffered by the action of a buffer.

Under these circumstances, according to an embodiment of the present invention, pyrophosphoric acid formed as a result of a DNA extension reaction is enzymatically converted into a redox compound and the redox compound is electrically detected. An electrochemically active material is immobilized to a surface of an electrode (measuring electrode) through an insulating molecule to reduce variation in potential due to a reaction or adsorption of a foreign substance on the surface of the electrode. The electrochemically active material to be immobilized is optimized according to the redox compound to be detected. According to another embodiment of the present invention, an insulating-gate field-effect transistor is used as a potentiometer, which field-effect transistor is arranged on the same substrate as the measuring electrode. To integrate detectors at a higher density so as to carry out DNA sequencing at a high throughput, an integrated circuit is prepared by arranging measuring electrodes and insulating-gate field-effect transistors on the same substrate, and data are converted into serial data using the integrated circuit.

According to an embodiment of the present invention, pyrophosphoric acid is converted into a redox compound and a variation in concentration of the redox compound is detected as a variation in surface potential. Thus, sensors can be used at a higher density, and smaller amounts of samples can be analyzed without reducing the detection sensitivity. Measurements using dATP, more inexpensive than dATPαS, can be conducted, because ATP is not directly involved in the reaction system, and background signals due to dATP do not occur. The signal intensity herein does not decrease even with a proceeding extension reaction of a double-stranded DNA, because the signal intensity does not vary depending on the extension reaction site of the double-stranded DNA. In addition, this process is resistant to effects of buffers and reagents, because pyrophosphoric acid as a product of a DNA extension reaction is converted into a redox compound. A leakage current causing the reduction in sensitivity can be reduced, and, concurrently, a variation in potential due to a reaction and adsorption of a foreign substance on the surface of the electrode can be reduced by immobilizing an electrochemically active material to the surface of the electrode through an insulating molecule. The sensitivity can be increased by selecting an electrochemically active material to be immobilized according to a redox compound to be detected. A downsized system can be constructed at low cost by using, as a potentiometer, an insulating-gate field-effect transistor arranged on the same substrate as a measuring electrode. For a higher throughput of the system, the number of interconnections can be reduced and the system can have a simplified configuration by converting data from the insulating-gate field-effect transistor arranged on the same substrate as the measuring electrode into serial data in an integrated circuit arranged on the same substrate.

DETAILED DESCRIPTION OF THE PREFERRED EMBODIMENTS

Some embodiments of the present invention will be illustrated below with reference to the attached drawings.

Figure 1:
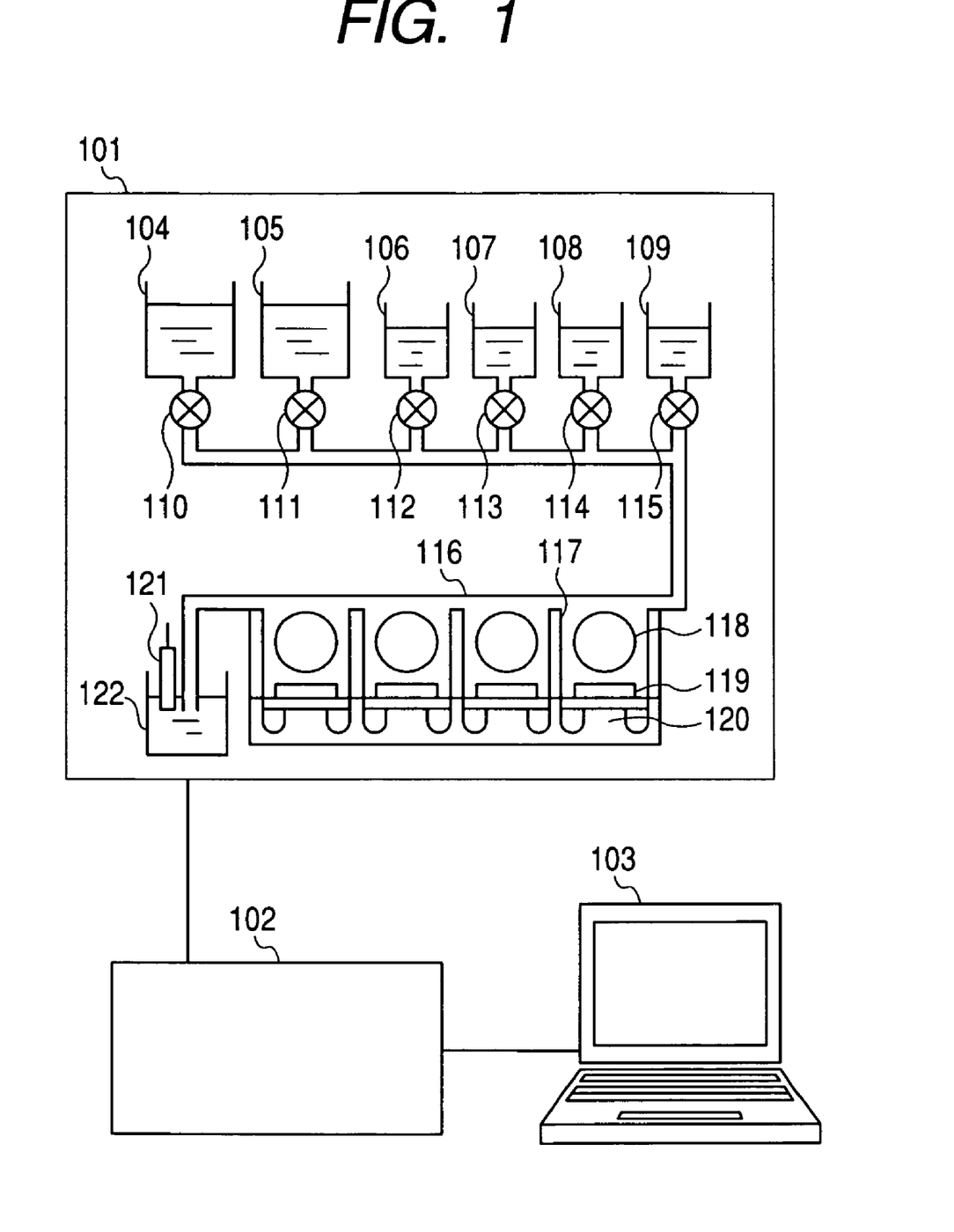
FIG. 1 is a block diagram illustrating a DNA analysis system according to an embodiment of the present invention.

FIG. 1 is a block diagram illustrating a nucleic acid sequence analysis system according to an embodiment of the present invention. The analysis system according to this embodiment includes a measuring unit 101, a signal processing circuit 102, and a data processor 103. The measuring unit 101 includes a washing buffer vessel 104, a reaction buffer vessel 105, a dATP solution vessel 106, a dTTP solution vessel 107, a dGTP solution vessel 108, a dCTP solution vessel 109, a washing buffer supply valve 110, a reaction buffer supply valve 111, a dATP solution supply valve 112, a dTTP solution supply valve 113, a dGTP solution supply valve 114, a dCTP solution supply valve 115, a measuring cell 116, separators 117, beads 118, measuring electrodes 119, field-effect transistors 120, a reference electrode 121, and a discharge liquid vessel 122. The supplies of the respective solutions can be controlled by opening or closing the respective valves. The measuring cell 116 is partitioned to two or more (n) spaces by the separators 117. Each space includes one set of a bead 118, a measuring electrode 119, and a field-effect transistor 120. A probe DNA is immobilized to a surface of each bead 118, and a target DNA hybridizes with the probe DNA. In case that a sample is RNA, complimentary DNA (cDNA) of the RNA can be used. The beads may be, for example, generally-used polystyrene beads or magnetic beads. The surfaces of the beads are modified typically with carboxyl group, amino group, maleimido group, hydroxyl group, biotin, or avidin. Probe DNAs modified typically with a corresponding moiety such as amino group, carboxyl group, SH group, silanol group, avidin, or biotin are immobilized thereto. Fine gold particles, for example, may be used instead of beads. In this case, probe DNAs modified with a functional group can be immobilized by coating the fine gold particles with a molecule having a corresponding functional group. An electrochemically active material is immobilized to a surface of the measuring electrode 119 through (by the interposition of) an insulating molecule. The measuring electrode 119 may be a noble metal electrode, such as a gold electrode, or a carbon electrode. The reference electrode 121 is in contact with a solution in the discharge liquid vessel 122.

A washing buffer in the washing buffer vessel 104 herein was reduced nicotinamide adenine dinucleotide (NADH). A reaction buffer in the reaction buffer vessel 105 herein was a solution of DNA polymerase, pyruvate orthophosphate dikinase (PPDK), lactate dehydrogenase, phosphoenolpyruvic acid (PEP), adenosine monophosphate (AMP), and NADH in Tris-HCl buffer. Solutions in the dATP solution vessel 106, dTTP solution vessel 107, dGTP solution vessel 108, and dCTP solution vessel 109 were solutions of dATP, dTTP, dGTP, and dCTP, respectively, in Tris-HCl buffer. The reference electrode 121 herein was a Ag/AgCl reference electrode containing a saturated potassium chloride solution as an internal fluid. However, any reference electrode will do, as long as it has a variation in potential sufficiently smaller than the variation in potential corresponding to one base extension.

In the present embodiment, the reference electrode 121 was in contact with a solution in the discharge liquid vessel 122. However, the reference electrode 121 can be arranged at any position in the system as long as it is in contact with a solution in a measuring cell. The beads herein were polystyrene beads having a diameter of 50 μm and containing terminal carboxyl groups. A probe DNA was immobilized to the beads by mixing the beads with an amino-modified probe DNA and adding N-hydroxysuccinimide (NHS) and 1-ethyl-3-(3-dimethylaminopropyl)carbodiimide (EDC) thereto to thereby chemically bind the probe DNA with the beads. A gold electrode was used as the measuring electrode 119. The insulating molecule and the electrochemically active material used herein were 11-amino-1-undecanethiol (11-AUT) and pyrroloquinoline quinone (PQQ), respectively. A self-assembled monolayer of 11-AUT was formed on the gold electrode using a solution of 11-AUT. A mixture of PQQ, NHS, and EDC was added dropwise onto this electrode, a reaction was conducted overnight to immobilize PQQ to the electrode through a chemical bond between an amino group of 11-AUT and a carboxyl group of PQQ.

Figure 2:
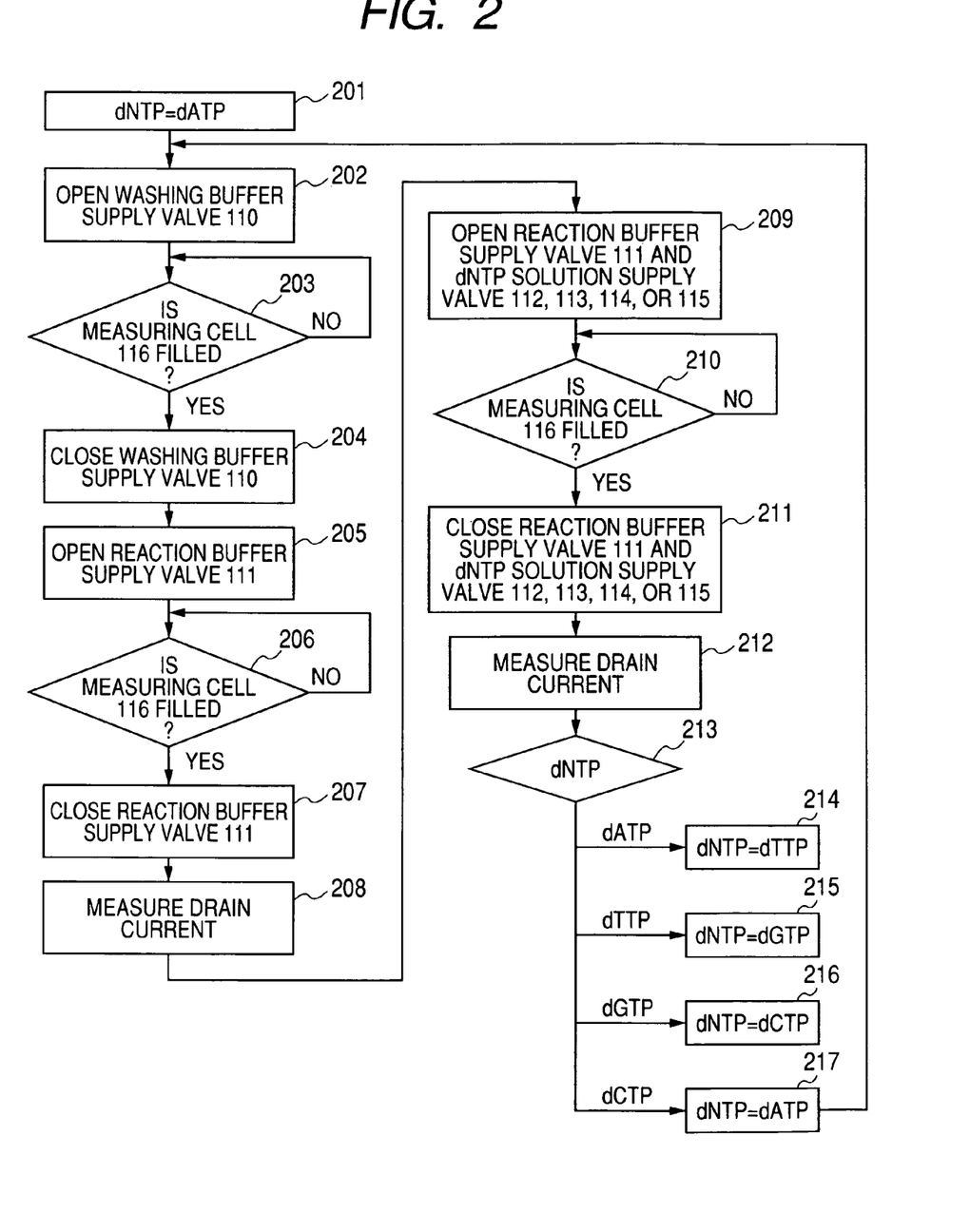
FIG. 2 is a flow chart illustrating a DNA analysis method using a DNA analysis system according to an embodiment of the present invention.

Procedural steps are illustrated in FIG. 2 by way of example. Initially, the washing buffer supply valve 110 was opened (202), the measuring cell 116 was filled with a washing buffer (potential initializer)(203), and then the washing buffer supply valve 110 was closed (204). By this procedure, the electrochemically active material immobilized to the surface of the measuring electrode 119 was reduced. Next, the reaction buffer supply valve 111 was opened (205), the measuring cell was filled with the reaction buffer (206), and the reaction buffer supply valve 111 was then closed (207). A constant voltage $V_G$ was applied to the reference electrode 121, and drain currents of respective field-effect transistors were measured (208). The respective measured drain currents were indicated as $I_D$ (1, n) ("n" is a number assigned to a field-effect transistor). The reaction buffer supply valve 111 and the dNTP solution supply valve 112, 113, 114, or 115 were opened (209), the measuring cell 116 was filled with a mixture of the reaction buffer and the dNTP solution (210), and the reaction buffer supply valve 111 and the dNTP solution supply valve 112, 113, 114, or 115 were closed (211). As the dNTP were sequentially used dATP, dTTP, dCTP, and dGTP (201, 213 to 217). A constant voltage $V_G$ was applied to the reference electrode 121, and drain currents of the respective field-effect transistors were measured (212). The measured drain currents herein were indicated as $I_D(2, n)$ ("n" is a number assigned to a field-effect transistor), in which $\Delta I_D$ (n)=$I_D(2, n)-I_D(1, n)$, in which $\Delta I_D$ represents a variation in drain current of a field-effect transistor as a result of supply of a dNTP. The procedure was returned to the operation of opening the washing buffer supply valve 110 (202), and measurements were repeatedly conducted sequentially using dATP, dTTP, dCTP, and dGTP as a dNTP.

Alternatively, dATP, dTTP, dGTP, and dCTP may be dissolved in a reaction buffer in the reaction buffer vessel 105 for use as a dATP solution in the dATP solution vessel 106, a dTTP solution in the dTTP solution vessel 107, a dGTP solution in the dGTP solution vessel 108, and a dCTP solution in the dCTP solution vessel 106, respectively. In this case, the operation of opening the dNTP solution supply valve 112, 113, 114, or 115 is employed instead of the operation of opening the reaction buffer supply valve 111 and the dNTP solution supply valve 112, 113, 114, or 115 (209). Any order of dATP, dTTP, dCTP, and dGTP used as the dNTP will do, as long as each dNTP is used every four times. Instead of a dNTP, any substance will do, as long as it is taken into a synthesis reaction of a double-stranded DNA by the catalysis of a DNA synthetase in a manner specific to a base sequence. An example of the substance is an analogue except with sulfur atom substituting a part of molecule (dNTPαS, in which the 4'-position of pentose is substituted with sulfur (N. Inoue et. al., Nucleic Acids Research, 3476-3483, 34, 2006)). The washing buffer is used for initializing the surface potential of an electrode which has been varied by the action of a redox compound converted from pyrophosphoric acid. In this embodiment, the surface potential is increased due to an extension reaction, but it is reduced by the action of a reducing material in the washing buffer. Thus, another measurement of an extension reaction can be conducted. A solution containing a reducing material such as a thiol compound instead of the above-mentioned material may be used. The surface potential may be reduced in some combinations of a redox compound and an enzyme in the reaction buffer. In this case, the washing buffer may be a solution containing an oxidant such as hydrogen peroxide or potassium ferrocyanide.

Figure 3:
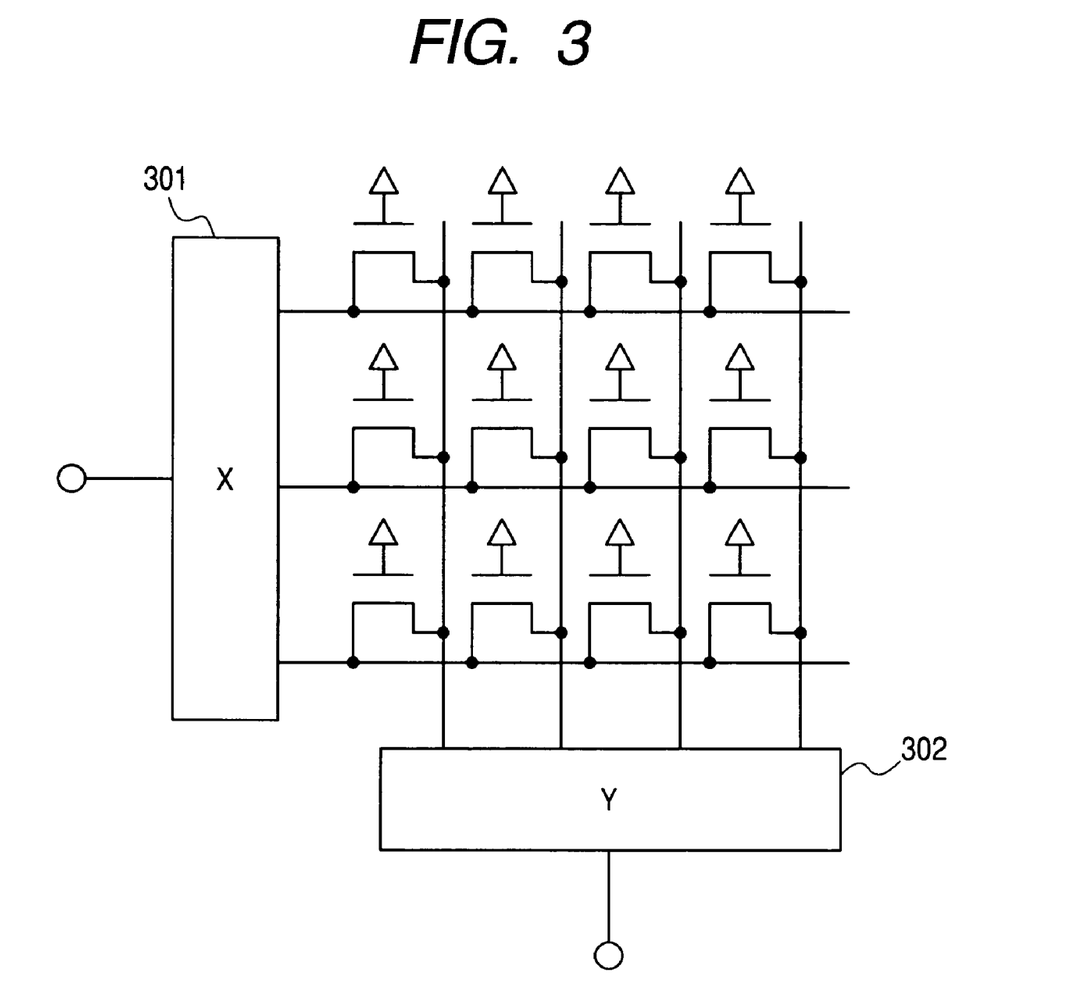
FIG. 3 is a block diagram illustrating an example of a circuit diagram of a FET sensor for use in a DNA analysis system according to an embodiment of the present invention.

FIG. 3 is a circuit diagram illustrating a field-effect transistor for use in a nucleic acid sequence analysis system according to an embodiment of the present invention. The circuits shown in the circuit diagram are preferably arranged or integrated on one substrate. Field-effect transistors are arrayed in a matrix, and a field-effect transistor whose source/drain current-potential characteristics are to be read out can be selected using an X-selector 301 and a Y-selector 302. For example, when source/drain current-potential characteristics of a field-effect transistor which is third from the left and second from the top are to be read out, interconnections the second from the top and the third from the left are connected using the X-selector and the Y-selector, respectively. Thus, the number of interconnections for measuring potentials of a multiplicity of electrodes can be reduced.

A process of chemical reactions for detecting an extension reaction as a variation in potential in sequence analysis using a nucleic acid sequence analysis system according to an embodiment of the present invention will be illustrated below by way of example. A double-stranded DNA synthesis reaction on a bead yields pyrophosphoric acid. This reaction is catalyzed by a DNA polymerase.

Double-stranded DNA("*n*" base length)+
    dNTP→Double-stranded DNA("*n*+1" base
    length)+Pyrophosphoric acid

The formed pyrophosphoric acid is converted into pyruvic acid. This reaction is catalyzed by PPDK.

Pyrophosphoric acid+PEP+AMP→Pyruvic acid+
    ATP+Phosphoric acid

The formed pyruvic acid is converted into NAD. This reaction is catalyzed by lactate dehydrogenase.

Pyruvic acid+NADH→Lactic acid+NAD

The formed NAD oxidizes PQQ immobilized to the surface of the electrode.

PQQ(reduced)+NAD ⇔ PQQ(oxidized)+NADH

This reaction is an equilibrium reaction, and the ratio of oxidized PQQ to reduced PQQ is in accordance with the ratio of NAD to NADH.

Figure 4A:
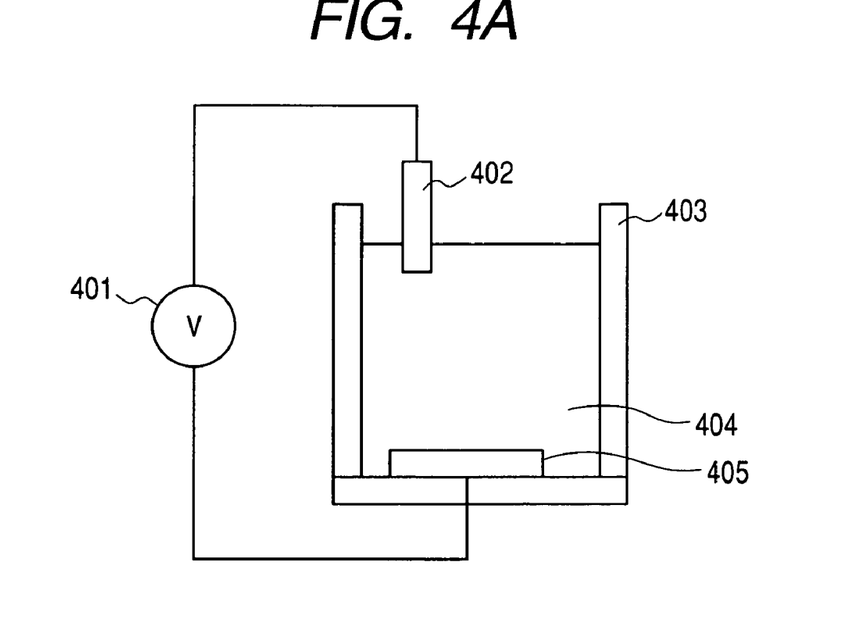
FIGS. 4A and 4B are explanatory diagrams of a system for evaluating the immobilization of an electrochemically active material to a surface of a measuring electrode through an insulating molecule.
Figure 4B:
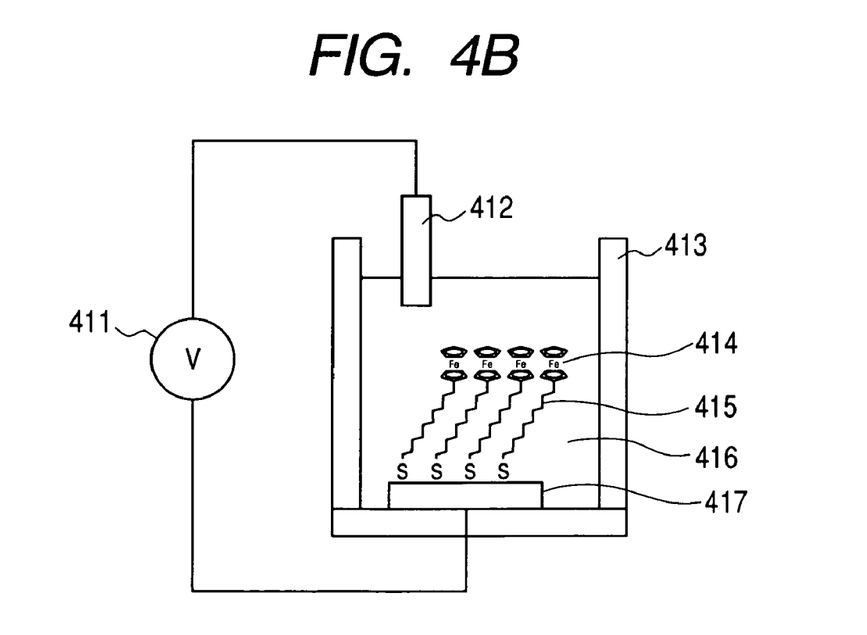

Effects of the immobilization of an electrochemically active material to a surface of a measuring electrode through an insulating molecule will be illustrated with reference to another embodiment. FIG. 4A illustrates an evaluation system for an untreated measuring electrode; and FIG. 4B illustrates an evaluation system for a measuring electrode bearing an electrochemically active material immobilized thereto through an insulating molecule. The evaluation system for an untreated measuring electrode includes a potentiometer 401, a reference electrode 402, and a measuring cell 403. The measuring cell 403 contains a measuring solution 404, a gold electrode 405, and the reference electrode 402. The evaluation system for a measuring electrode bearing an electrochemically active material immobilized thereto through an insulating molecule includes a potentiometer 411, a reference electrode 412, and a measuring cell 413. The measuring cell 413 contains a measuring solution 416, a gold electrode 417, and the reference electrode 412. The gold electrode 417 bears an electrochemically active material 414 immobilized thereto through an insulating molecule 415.

Figure 5:
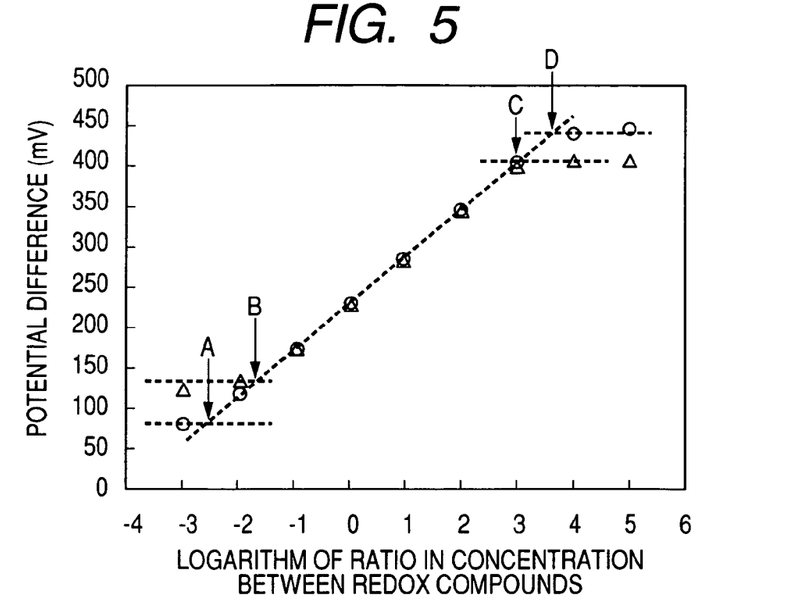
FIG. 5 is a diagram showing an effect of the immobilization of an electrochemically active material to a surface of a measuring electrode through an insulating molecule.

FIG. 5 shows how the potential difference between a reference electrode and a gold electrode varies depending on the logarithm of the ratio in concentration between redox compounds in the measuring solution (the logarithm of the ratio of the potassium ferricyanide concentration to the potassium ferrocyanide concentration). These data were measured using the evaluation systems in FIGS. 4A and 4B. In FIG. 5, a plot indicated by open triangle shows data measured by the evaluation system in FIG. 4A; and a plot indicated by open circles shows data measured by the evaluation system in FIG. 4B. The reference electrodes 402 and 412 used herein were each a Ag/AgCl reference electrode containing a saturated aqueous potassium chloride solution as an internal fluid. The electrochemically active material 414 immobilized through the insulating molecule 415 was 11-ferrocenyl-1-undecanethiol (11-FUT). The measuring solutions 404 and 416 were each a 0.1 M aqueous sodium sulfate solution containing potassium ferricyanide and potassium ferrocyanide in a total concentration of 10 μM. The measurements were conducted at 25° C. At logarithms of the ratio in concentration between redox compounds within a range of −1 to 3, both the plot indicated by open triangles and the plot indicated by open circles well fit the straight line of 58 mV, showing that a potential occurs according to the Nernst's equation. The plot indicated by open triangles, however, deviates from the straight line at logarithms of the ratio in concentration between redox compounds of −2 or less and 4 or more, the range of potentials fitting the straight line is 134 to 409 mV, and this corresponds to a range of concentrations of 4.7 digits. In contrast, the plot indicated by open circles shows a range of potentials fitting the straight line of 80 to 442 mV, and this corresponds to a range of concentrations of 6.2 digits. In other words, the dynamic range is increased by 1.5 digits by immobilizing an electrochemically active material to a measuring electrode through an insulating molecule.

When a measuring electrode does not have an insulating molecule immobilized thereto, the measuring electrode is not sufficiently insulated from a measuring solution. Accordingly, a leakage current on the surface of the measuring electrode inhibits the measuring electrode from detecting a trace variation in concentration of a target material to be measured. In contrast, by immobilizing an electrochemically active material to a measuring electrode through an insulating molecule, the measuring electrode is highly insulated from a measuring solution, and a leakage current on the surface of the measuring electrode is reduced. Thus, the measuring electrode can detect a trace variation of the target material to be measured. In this case, molecules of the electrochemically active material are preferably immobilized to the measuring electrode through molecules of the insulating molecule having identical lengths. Thus, the insulating property between the measuring electrode and the measuring solution can be maintained at satisfactory level, and variations in conditions of molecules of the electrochemically active material uniformly affect the surface potential of the measuring electrode.

Figure 6:
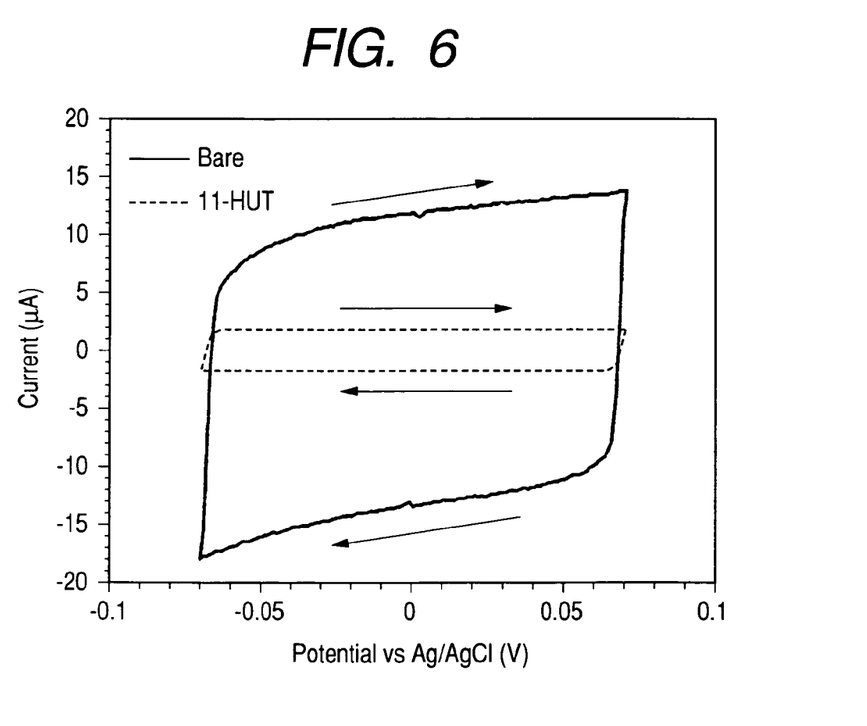
FIG. 6 is a diagram showing an effect of the immobilization of an electrochemically active material to a surface of a measuring electrode through an insulating molecule.

Effects of the immobilization of an electrochemically active material to a surface of a measuring electrode through an insulating molecule will be illustrated with reference to yet another embodiment of the present invention. FIG. 6 shows voltammograms measured using systems containing an untreated gold electrode and a gold electrode bearing an immobilized insulating molecule, respectively. The poten- tiostat used herein was the Electrochemical Analyzer ALS Model 611B. The reference electrode was a Ag/AgCl reference electrode containing a saturated aqueous potassium chloride solution as an internal fluid. The counter electrode was a platinum wire. The measuring solution was a 0.1 M aqueous sodium sulfate solution. In the voltammograms, a current varying in a scanning direction represents an electrostatic capacity, and a slope versus an applied potential represents a resistance of the electrode surface. The gold electrode bearing 11-hydroxy-1-undecanethiol (11-HUT) as an immobilized insulating molecule showed a smaller slope of the current versus the applied potential than that of the untreated gold electrode. This means that the electrode surface has an increased insulating property by immobilizing an insulating molecule to the electrode surface. In addition, the gold electrode bearing 11-HUT as an immobilized insulating molecule showed a smaller absolute value of the current than that of the untreated gold electrode. This is because the untreated gold electrode has a layer called "electric double layer" having a thickness substantially corresponding to one molecule and thereby shows a large electrostatic capacity of about 14 $\mu F/cm^2$; but, in contrast, the gold electrode bearing the immobilized insulating molecule has an insulating layer having a thickness of about 2 nm corresponding to the length of the insulating molecule and thereby shows a decreased electrostatic capacity of about 2.3 $\mu F/cm^2$. Thus, by immobilizing an insulating molecule to a surface of an electrode, the electrode has an increased surface resistance and thereby shows a decreased electrostatic capacity. As a result, the leakage current is reduced, a charging current is also reduced, and the measuring electrode can detect a further smaller variation in concentrations of redox compounds.

Figure 7:
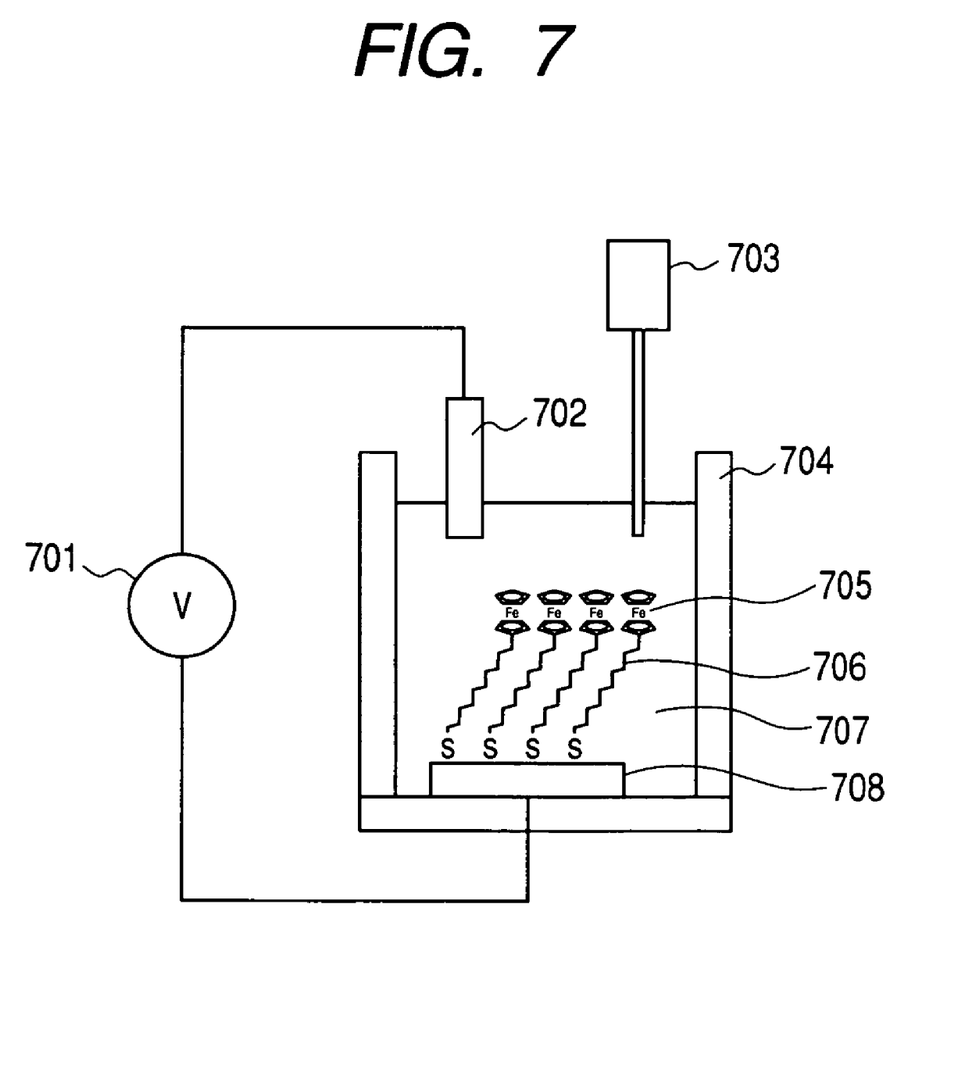
FIG. 7 is an explanatory diagram of a system for evaluating the immobilization of an electrochemically active material to a surface of a measuring electrode through an insulating molecule.

Effects of the immobilization of an electrochemically active material to a surface of a measuring electrode through an insulating molecule will be illustrated with reference to still another embodiment of the present invention. FIG. 7 illustrates an evaluation system for a measuring electrode bearing an electrochemically active material immobilized thereto through an insulating molecule. This evaluation system includes a potentiometer 701, a reference electrode 702, a sample solution injector 703 that supplies a sample solution containing a target material, and a measuring cell 704. The measuring cell 704 contains a measuring solution 707. A gold electrode 708 and the reference electrode 702 are arranged in the measuring solution 707. The gold electrode 708 bears an electrochemically active material 705 immobilized thereto through an insulating molecule 706.

Figure 8:
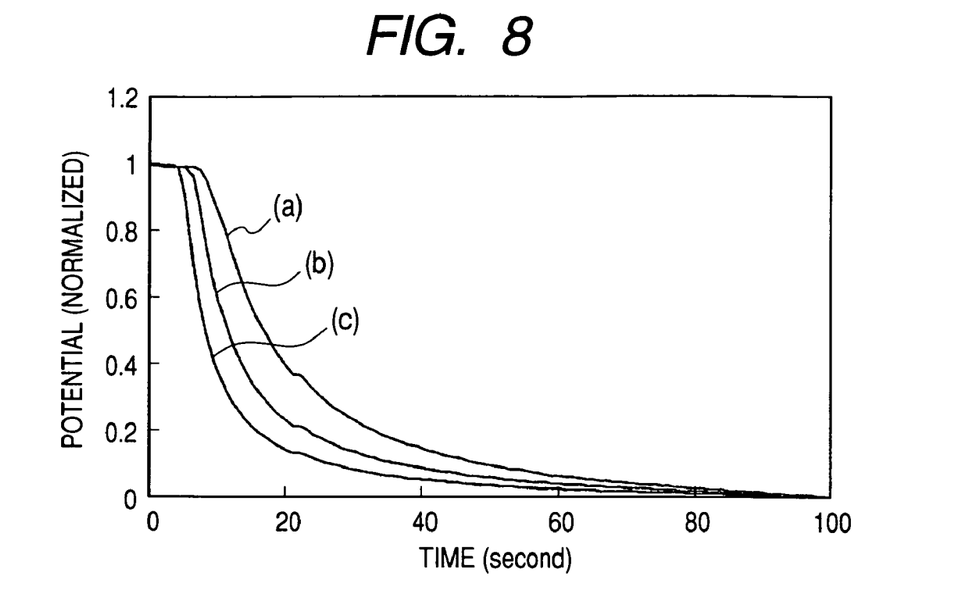
FIG. 8 is a diagram showing an effect of the immobilization of an electrochemically active material to a surface of a measuring electrode through an insulating molecule.

FIG. 8 shows how the potential difference between the reference electrode and the gold electrode varies depending on the time elapsed from the injection of a target material, which was measured using the evaluation system in FIG. 7. The reference electrode 702 used herein was a Ag/AgCl reference electrode containing a saturated aqueous potassium chloride solution as an internal fluid. The electrochemically active material 705 immobilized through the insulating molecule 706 was (a) 6-ferrocenyl-1-hexanethiol, (b) 8-ferrocenyl-octanethiol, and (c) 11-FUT, respectively. The sample solution in the sample solution injector was an aqueous potassium ferrocyanide solution. The measuring solution 807 was a 0.1 M aqueous sodium sulfate solution. In FIG. 8, the abscissa indicates the time elapsed from the injection of the sample solution, and the ordinate indicates the potential difference between the reference electrode and the gold electrode. The potential difference was normalized by defining the potential immediately before the injection of the sample solution as 1 and defining the potential 100 seconds after the injection as 0. The time for the potential to be 0.1 after the injection of the sample solution, namely, the time for the variation in potential to be 90% was defined as a relaxation time. The relaxation times in (a), (b), and (c) satisfy the following condition: (a)>(b)>(c). Specifically, the relaxation time decreases with an increasing length of the insulating molecule 706. The insulating property between the measuring electrode and the measuring solution increases with an increasing length of the insulating molecule 706. In other words, the response speed increases with an increasing insulating property.

Figure 9:
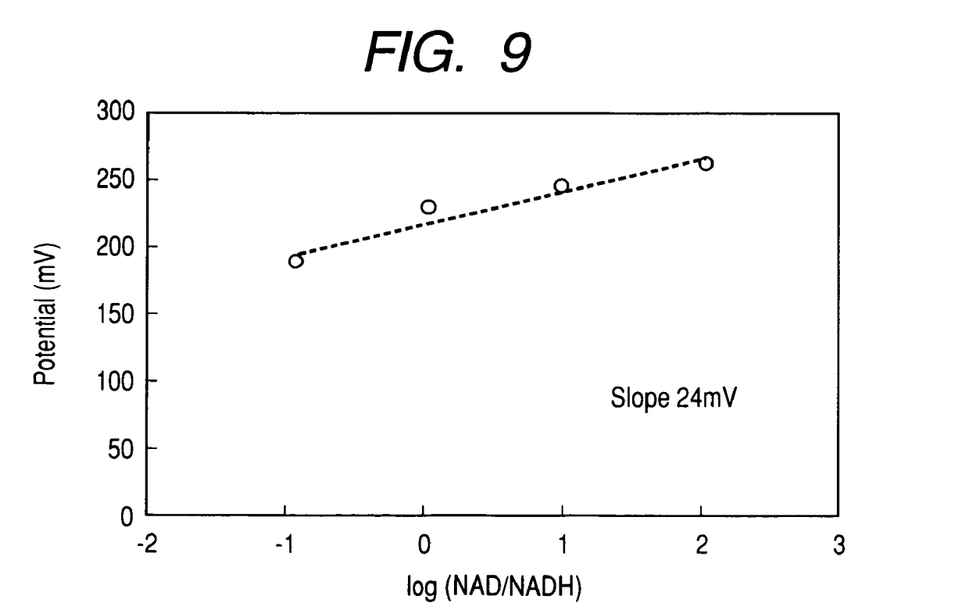
FIG. 9 is a diagram showing an effect of the immobilization of an electrochemically active material to a surface of a measuring electrode through an insulating molecule.
Figure 10:
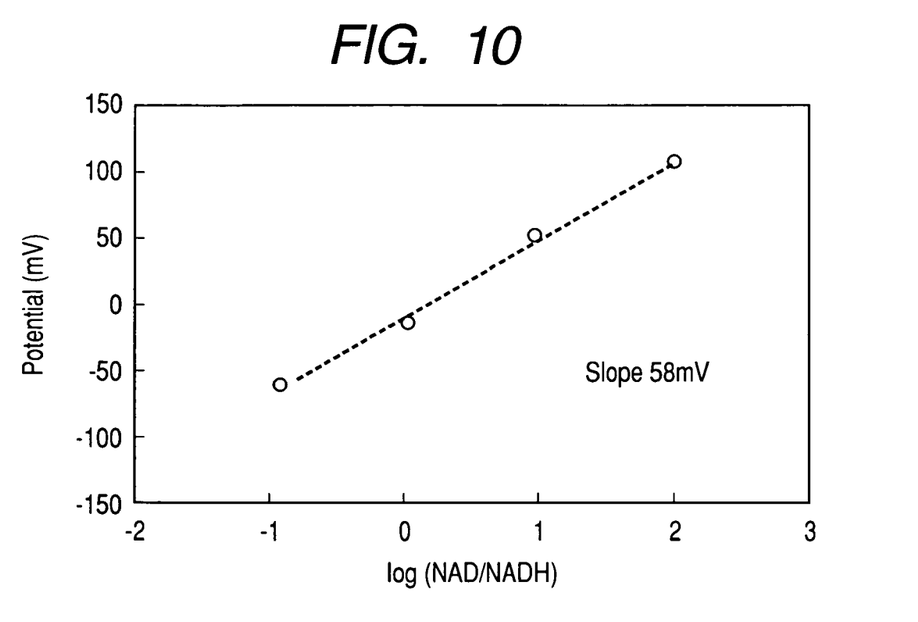
FIG. 10 is a diagram showing an effect of the immobilization of an electrochemically active material to a surface of a measuring electrode through an insulating molecule.

The sensitivity can be improved by selecting an electrochemically active material to be immobilized according to a redox compound to be used. This will be explained with reference to another embodiment of the present invention. FIG. 9 shows data of the measurement of NAD and NADH as redox compounds using an electrode including a gold electrode bearing 11-FUT immobilized on its surface (1-FUT-immobilized electrode). FIG. 10 shows data of the measurement of NAD and NADH as redox compounds using an electrode including a gold electrode bearing 11-amino-1-undecanethiol immobilized on its surface and further bearing pyrroloquinoline quinone (PQQ) immobilized thereon (PQQ-immobilized electrode). The 11-FUT-immobilized electrode has a slope sensitivity of 24 mV, and the PQQ-immobilized electrode has a slope sensitivity of 58 mV.

The above-mentioned reactions will be theoretically considered. When the 11-FUT-immobilized electrode is used, the following equilibrium reaction establishes between the immobilized ferrocene and NAD/NADH in the solution.

2 Ferrocene(reduced)+NAD ⇔ 2 Ferrocene(oxidized)+NADH

Accordingly, the following equation establishes:

[Equation 1]

$$\left(\frac{[\text{Ferrocene(oxidized)}]}{[\text{Ferrocene(reduced)}]}\right)^2 = \frac{[NAD]}{[NADH]} \quad (1)$$

[Ferrocene (oxidized)]: Oxidized ferrocene concentration
[Ferrocene (reduced)]: Reduced ferrocene concentration
[NAD]: NAD concentration
[NADH]: NADH concentration The surface potential E of the electrode is theoretically determined from the ratio between oxidized form and reduced form of the electrochemically active material immobilized to the electrode surface, according to the following Nernst's equation:

[Equation 2]

$$E = E^0 + \frac{RT}{nF} \log \frac{[Ox]}{[Red]} \quad (2)$$

$E^0$: Standard oxidation-reduction potential
R: Gas constant
T: Absolute temperature
n: Number of electrons to be exchanged
F: Faraday constant

[Red]: Concentration of reduced electrochemically active material

[Ox]: Concentration of oxidized electrochemically active material

Equation (1) is substituted into Equation (2) to give Equation (3):

[Equation 3]

$$E = E^0 + \frac{RT}{2F}\log\frac{[NAD]}{[NADH]} \quad (3)$$

The slope sensitivity to the NAD and NADH concentrations is thus determined as 30 mV at 25° C. The measured slope sensitivity was smaller than this theoretical value. This is probably because a redox reaction between ferrocene and NAD/NADH has a low reaction rate and thereby did not reach an equilibrium state.

When the PQQ-immobilized electrode is used, the following equilibrium reaction establishes between the immobilized PQQ and NAD/NADH in the solution.

PQQ(reduced)+NAD ⇔ PQQ+NADH

Accordingly, the following equation establishes:

[Equation 4]

$$\frac{[PQQ(\text{oxidized})]}{[PQQ(\text{reduced})]} = \frac{[NAD]}{[NADH]} \quad (4)$$

[PQQ (oxidized)]: Oxidized PQQ concentration
[PQQ (reduced)]: Reduced PQQ concentration Equation (4) is substituted into Equation (2) to give

[Equation 5]

$$E = E^0 + \frac{RT}{F}\log\frac{[NAD]}{[NADH]} \quad (5)$$

The slope sensitivity to the NAD and NADH concentrations is thus determined as 59 mV at 25° C. The measured slope sensitivity was substantially equal to the theoretical value, indicating that a redox reaction between PQQ and NAD/NADH reached an equilibrium state when the potential was measured, because it has a sufficiently high reaction rate. The sensitivity can be improved by selecting an electrochemically active material to be immobilized to a surface of an electrode according to a redox compound to be used in this manner. Suitable combinations for electrically detecting pyrophosphoric acid will be illustrated below, by way of example.

In case that a Ferrocene is the immobilized electrochemically active molecule, the metal complex is better for the redox compound, especially a transition metal, specifically whose d-orbitals are not full, for example Fe, Ru, and Co.

TABLE 1

| Immobilized electrochemically active molecule | Redox compound | Reaction system (example) |
|---|---|---|
| Ferrocene | Ferricyanide, Ferrocyanide | Pyrophosphoric acid + Fructose 6-phosphate $\xrightarrow{\text{Fructose-6-phosphate\_kinaze}}$ Fructose 1,6-dihosphate + Phosphoric acid<br><br>Fructose 1,6-dihosphate $\xrightarrow{\text{Aldolase}}$ Glyceraldehyde-3-phosphate + Dihydroxyacetone phosphate<br><br>Glyceraldehyde-3-phosphate + NAD + Phosphoric acid $\xrightarrow{\text{Glyceraldehyde-3-phosphate\_dehydrogenase}}$ Glycerate-1,3-diphosphate + NADH<br><br>NADH + 2 Ferricyanide $\xrightarrow{\text{Diaphorase}}$ NAD + 2 Ferrocyanide |
| PQQ | NAD, NADH | Pyrophosphoric acid + PEP + AMP $\xrightarrow{\text{PPDK}}$ Pi + Pyruvic acid + ATP<br><br>Pyruvic acid + NADH $\xrightarrow{\text{Lactate\_dehydrogenasse}}$ Lactic acid + NAD |

Figure 11:
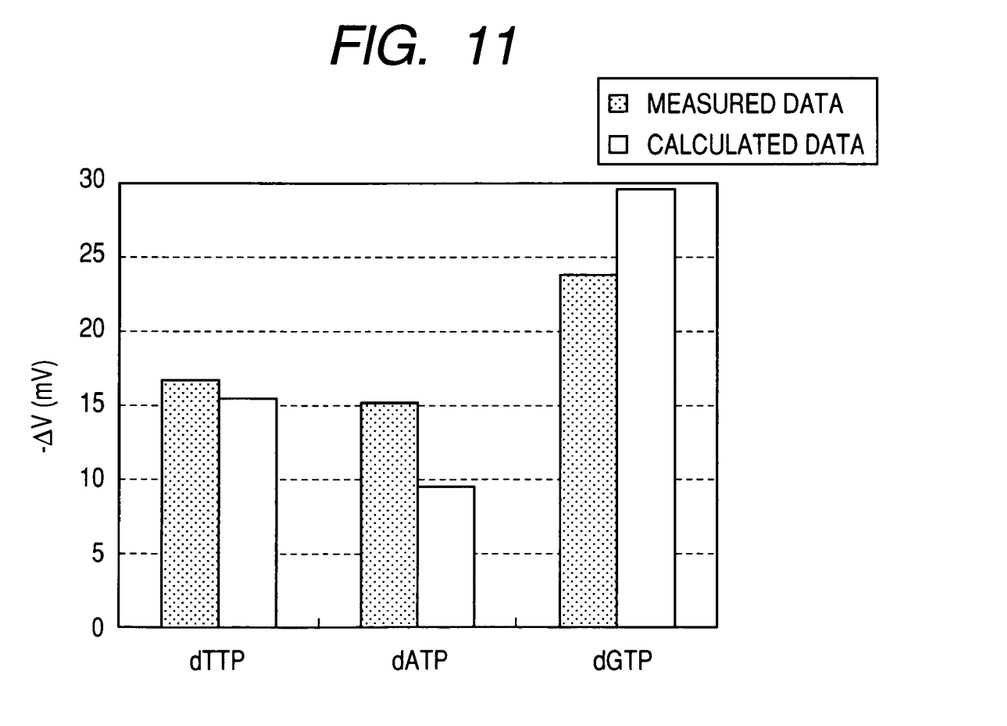
FIG. 11 is a graph showing data of an analysis using a DNA analysis system according to an embodiment of the present invention by way of example.

FIG. 11 shows measured data in detection of an extension reaction of DNA, and calculated data thereof. To a solution were sequentially added dTTP, dATP, and dGTP (each 5 mM, 1 μL). The solution contained a mixture of a double-stranded DNA (10 μM, 50 μL), DNA polymerase (50 U/ml, 1 μL), fructose 6-phosphate kinase (0.5 U/ml, 1 μL), aldolase (50 U/ml, 1 μL), glyceraldehyde-3-phosphate dehydrogenase (1 U/ml, 1 μL), diaphorase (10 U/ml, 1 μL), fructose 6-phosphate (90 mM, 1 μL), NAD (3 mg/ml, 1 μL), and potassium ferricyanide (10 mM, 5 μL). A primer DNA and a sample DNA used as the double-stranded DNA had the following sequences:

Primer DNA:
(SEQ ID 1)
3'-CACAC TCACA GTTTT CACTT-5'

Sample DNA:
(SEQ ID 1)
3'-GCATA CACTA AAGTG AAAAC TGTGA GTGTG-5'

When dTTP was added, a single-base extension reaction occurred by the action of a DNA polymerase. This is because the base at position 10 from the 3' end of the sample DNA is A (adenine). Pyrophosphoric acid formed as a result of the extension reaction caused reduction of ferricyanide to yield ferrocyanide according to the following reactions:

Pyrophosphoric acid+Fructose 6-phosphate→Fructose 1,6-diphosphate+Phosphoric acid Fructose 1,6-diphosphate→Glyceraldehyde-3-phosphate+Dihydroxyacetone Glyceraldehyde-3-phosphate+NAD+Phosphoric acid→Glycerate-1,3-diphosphate+NADH NADH+2 Ferricyanide→NAD+2 Ferrocyanide The formation of ferrocyanide caused a variation in surface potential of the electrode. As a result, a decrease in potential of 16.7 mV was observed (FIG. 11). Next, dATP was added, and a single-base extension reaction occurred. This is because the base at position 9 from the 3' end of the sample DNA is T (thymine). This extension reaction caused a decrease in potential of 15.1 mV as observed in the same manner as above. Next, dGTP was added. As a result, the solution contained dATP, dTTP, and dGTP as dNTPs, and there occurred extension reactions of GTGTATG, which is a complementary sequence of the base sequence CATACAC at positions 2 to 8 from the 3' end of the sample DNA, except for the base G at the 3' end. The extension reactions of the seven bases caused a decrease in potential of 23.8 mV.

The decrease in potential will be theoretically considered. When the solution has a ferrocyanide concentration "x", a potential of $E_0 - 59 \log x$ occurs on the surface of the electrode at 25° C. according to the Nernst's equation. When ferrocyanide is formed in a concentration of $\Delta x$ as a result of a single-base extension reaction, and ferrocyanide has a concentration of $c_0$ before the extension reaction, ferrocyanide concentrations at respective points of time are as follows:

Before extension reaction: $c_0$
After addition of dTTP: $c_0 + \Delta x$
After addition of dATP: $c_0 + 2\Delta x$
After addition of dGTP: $c_0 + 9\Delta x$ Accordingly, potentials on surface of the electrode at the respective points of time are as follows:

Before extension reaction: $E_0 - 59 \log(c_0)$
After addition of dTTP: $E_0 - 59 \log(c_0 + \Delta x)$
After addition of dATP: $E_0 - 59 \log(c_0 + 2\Delta x)$
After addition of dGTP: $E_0 - 59 \log(c_0 + 9\Delta x)$ Consequently, variations in potential are:

Addition of dTTP: $59 \log(c_0 + \Delta x) - 59 \log(c_0)$
Addition of dATP: $59 \log(c_0 + 2\Delta x) - 59 \log(c_0 + \Delta x)$
Addition of dGTP: $59 \log(c_0 + 9\Delta x) - 59 \log(c_0 + 2\Delta x)$ When fitting was conducted, an optimum solution was obtained at $\Delta x$ of $0.83c$ (FIG. 11). The calculated data satisfactorily meet with the measured data, showing that pyrophosphoric acid formed as a result of extension reactions of the double-stranded DNA by adding respective dNTPs was detected as variations in potential.

Figure 12:
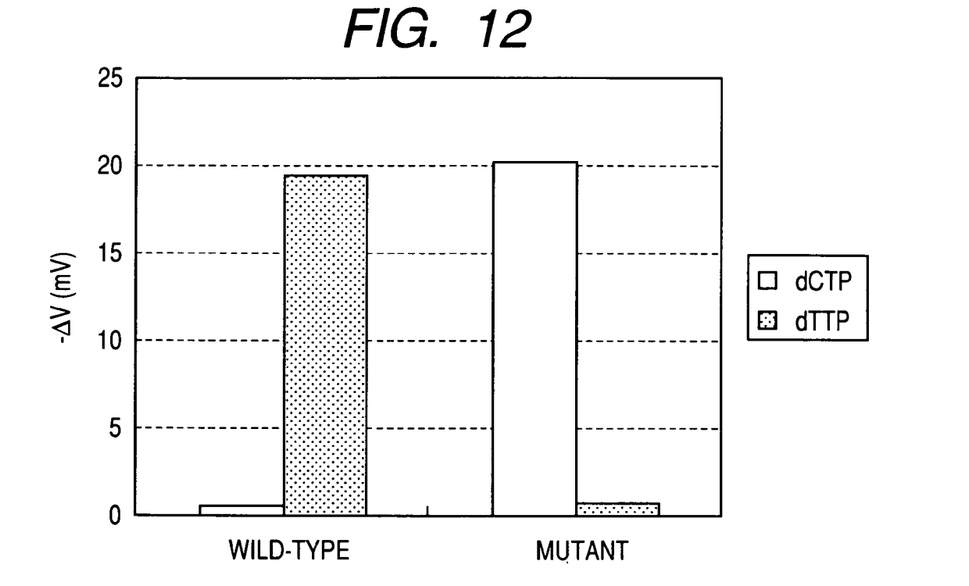
FIG. 12 is a graph showing how a single nucleotide polymorphism is detected.

SNPs (single nucleotide polymorphisms) can be detected in the same manner. Specifically, dCTP and dTTP (each 5 mM, 1 μL) were sequentially added to a solution containing a double-stranded DNA (50 μM, 50 μL), DNA polymerase (50 U/ml, 1 μL), fructose 6-phosphate kinase (0.5 U/ml, 1 μL), aldolase (50 U/ml, 1 μL), glyceraldehyde-3-phosphate dehydrogenase (1 U/ml, 1 μL), diaphorase (10 U/ml, 1 μL), fructose 6-phosphate (90 mM, 1 μL), NAD (3 mg/ml, 1 μL), and potassium ferricyanide (10 mM, 5 μL). A primer DNA and sample DNAs used as the double-stranded DNA had the following sequences:

Primer DNA:
(SEQ ID 1)
3'-CACAC TCACA GTTTT CACTT-5'

Sample DNA (wild-type):
(SEQ ID 2)
3'-GCATA CACTA AAGTG AAAAC TGTGA GTGTG-5'

Sample DNA (mutant):
(SEQ ID 3)
3'-GCATA CACTG AAGTG AAAAC TGTGA GTGTG-5'

Measurements were conducted on a combination of the primer DNA and the sample DNA (wild-type) and on a combination of the primer DNA and the sample DNA (mutant), respectively. With reference to FIG. 12, when the primer DNA and the sample DNA (wild-type) were used in combination, decreases in potential of 1 mV or less and 19.5 mV were observed by adding dCTP and dTTP, respectively. In contrast, when the primer DNA and the sample DNA (mutant) were used in combination, decreases in potential of 20.2 mV and 1 mV or less were observed by addition of dCTP and dTTP, respectively. These results reflect that, when the primer DNA and the sample DNA (wild-type) are used in combination, an extension reaction occurs not by the addition of dCTP but by the addition of dTTP, and that when the primer DNA and the sample DNA (mutant) are used in combination, an extension reaction occurs not by the addition of dTTP but by the addition of dCTP. By using these, SNPs can be detected.

When smaller volumes of samples are to be measured according to known technologies, signals may be lowered.

However, this can be prevented by measuring samples according to potentiometry. This will be theoretically considered as follows. How data according to luminometry (detection of photoluminescence) and potentiometry vary depending on the bead radius will be considered, assuming that a bead having a specific surface area (ratio of actual surface area to geometrical surface area) R and a radius r is arranged in a cubic cell having a side of 2r. The surface area of the bead is $4\pi r^2 R$ and is proportional to the square of the radius. According to luminometry, the signal intensity varies depending on the amount of DNA, namely, the surface area of the bead, and is proportional to the square of the bead radius when DNA is immobilized at a constant density. Accordingly, the signal intensity decreases with a decreasing volume of a sample to be measured according to luminometry. In contrast, the signal intensity according to potentiometry varies depending on the concentration of DNA. The volume of a sample solution is $(8 - 4/3\pi)r^3$ which is obtained by subtracting the volume of the bead $4/3\pi r^3$ from the volume of the cubic cell $8r^3$ and is proportional to the cube of the bead radius. Accordingly, the signal intensity according to potentiometry is proportional to the reverse number of the bead radius, because the concentration of DNA is inversely proportional to the bead radius when DNA is immobilized at a constant density. Consequently, the signal intensity increases with a decreasing volume of the sample to be measured according to potentiometry. Thus, the potentiometry is suitable for massive parallel analyses, because it is free from decrease in signal intensity even if smaller amounts of samples are measured.

Figure 13:
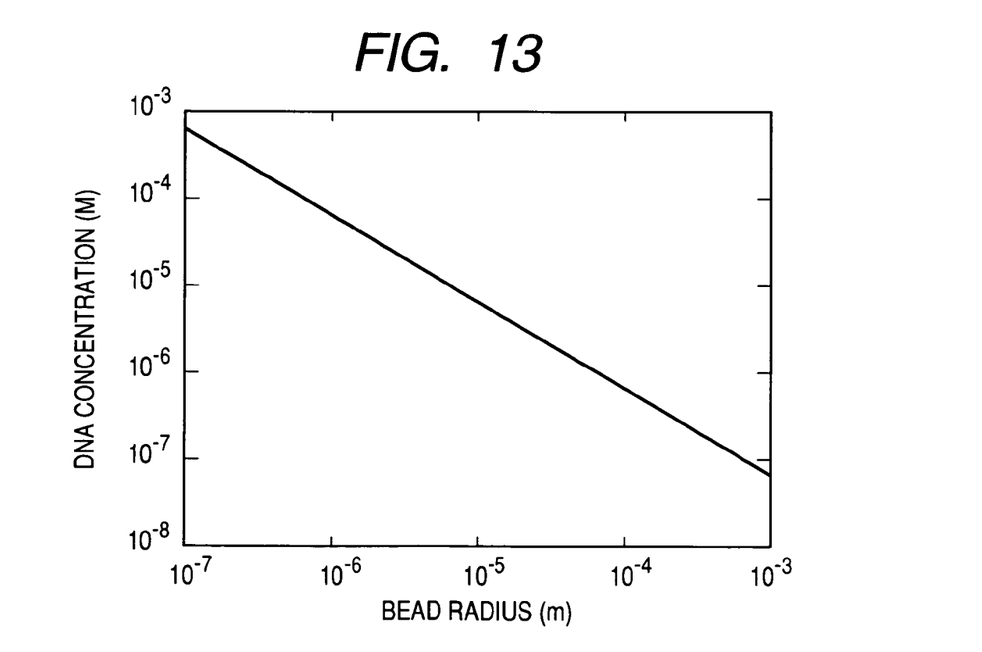
FIG. 13 is a graph showing how an apparent nucleic acid concentration varies depending on the radius of a bead bearing an immobilized nucleic acid.

Which bead radius is suitable will be considered below. The above-mentioned calculation shows that the volume of the sample solution is $(8-4/3\pi)r^3$. When DNA molecules are immobilized to the bead surface at intervals d, $4\pi r^2 R/d^2$ DNA molecules are immobilized to the bead surface. The DNA concentration in this case is $3R/\{(6-\pi)d^2 rN_A\}$ mol/m$^3$, and the relationship between the bead radius and the DNA concentration is determined as shown in FIG. 13 assuming that R is 1. When a minimum detectable concentration of a redox compound is $10^{-6}$ M, an extension reaction of one base can be detected at a bead radius of 70 μm or less, namely, at a bead diameter of 140 μm or less.

While preferred embodiments have been described, it should be understood by those skilled in the art that various modifications, combination, sub-combinations, and alternations may occur depending on design requirements and other factors insofar as they are within the scope of the appended claims or the equivalents thereof.

What is claimed is:

1. A DNA analysis system comprising:
   a vessel bearing an immobilized nucleic acid or containing an article bearing an immobilized nucleic acid, wherein the vessel is configured to receive a liquid;
   a reagent in the vessel, which converts pyrophosphoric acid formed as a result of an extension reaction of the nucleic acid into a redox compound;
   one or more measuring electrodes that are in contact with the liquid to be contained in the vessel for detecting the redox compound;
   an electrochemically active material that is immobilized to a surface of the measuring electrode through an insulating molecule;
   a reference electrode that is in contact with the liquid;
   one or more potentiometers that measure interface potentials of the one or more measuring electrodes;
   a first feeder that feeds dATP or an analogue thereof to the vessel;
   a second feeder that feeds dGTP or an analogue thereof to the vessel;
   a third feeder that feeds dCTP or an analogue thereof to the vessel;
   and a fourth feeder that feeds dTTP or an analogue thereof to the vessel.

2. The DNA analysis system of claim 1,
   wherein the article bearing the immobilized nucleic acid is a bead having a radius r and a specific surface area R,
   wherein molecules of the nucleic acid are immobilized on the bead at intervals d,
   wherein the one or more potentiometers each have a lower measuring limit in concentration of a redox compound $C_{lim}$, and the Avogadro's number is represented by $N_A$, and
   wherein the following condition is satisfied:

$r \leq 3RC_{lim}/\{(6-\pi)d^2 N_A\}$.

3. The DNA analysis system of claim 1, wherein the one or more potentiometers comprise one or more field-effect transistors.

4. The DNA analysis system of claim 3, wherein the measuring electrodes and the field-effect transistors are arranged on or above on the same substrate.

5. The DNA analysis system of claim 1, wherein the electrochemically active material comprises a quinone-containing molecule.

6. The DNA analysis system of claim 1, wherein the electrochemically active material comprises a ferrocene-containing material.

7. The DNA analysis system of claim 1, further comprising a cleaning unit that feeds a washing buffer into the vessel.

8. The DNA analysis system of claim 7, wherein the washing buffer comprises a redox compound for initialization.

9. The DNA analysis system of claim 1, further comprising a unit that feeds a reaction buffer into the vessel, wherein the reaction buffer comprises the reagent which converts pyrophosphoric acid formed as a result of an extension reaction of the nucleic acid into a redox compound.

* * * * *